United States Patent

Oi et al.

[11] 4,140,496
[45] Feb. 20, 1979

[54] s-TRIAZINE DERIVATIVES

[75] Inventors: Naobumi Oi, Kyoto; Hiroshi Takeda; Hiroo Shimada, both of Takatsuki, all of Japan

[73] Assignee: Sumitomo Chemical Company, Limited, Osaka, Japan

[21] Appl. No.: 792,252

[22] Filed: Apr. 29, 1977

[30] Foreign Application Priority Data

May 10, 1976 [JP] Japan .................................. 51/53682

[51] Int. Cl.² ............................................ B01D 15/08
[52] U.S. Cl. ............................................ 55/67; 55/386
[58] Field of Search ................. 55/67, 386; 210/31 C, 210/198 C; 23/232 C; 260/194, 208, 204

[56] References Cited

U.S. PATENT DOCUMENTS 2,891,941  6/1959  Fasciati et al. .................. 260/194 X
3,931,123  1/1976  Vacik et al. ...................... 210/31 C

Primary Examiner—John Adee
Attorney, Agent, or Firm—Birch, Stewart, Kolasch and Birch

[57] ABSTRACT

An optically active s-triazine derivative having at least two asymmetric carbon atoms of the general formula:

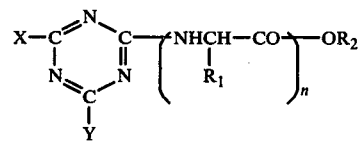

wherein n is 2 to 3; and X and Y are the same or different and are each a member selected from the group consisting of the groups:

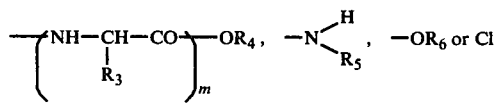

wherein m is 1 to 3; and $R_1$, $R_2$, $R_3$, $R_4$, $R_5$ and $R_6$ are the same or different and are each an alkyl having 1 to 12 carbon atoms, a cycloalkyl having 5 to 6 carbon atoms, phenyl or benzyl, and a gas chromatographic method for the resolution and analysis of the mixture of enantiomers having an —NH— group linked to an asymmetric carbon atom, comprising using said derivative as an optically active stationary phase for the gas chromatography.

6 Claims, 7 Drawing Figures

S-TRIAZINE DERIVATIVES

The present invention relates to novel optically active s-triazine derivatives. Further, the present invention relates to a gas chromatographic method for the resolution and analysis of a mixture of enantiomers having an —NH— group linked to the asymmetric carbon atom, which comprises using said novel optically active s-triazine derivative as a stationary phase for the gas chromatography.

Hitherto, various compounds have been well known which are useful as an optically active stationary phase for gas chromatography, for example, N-acylated polypeptide esters, carbonyl-bis-amino acid esters, amino acid amides (U.S. Pat. No. 3,494,105) and the like. Since, however, these compounds mostly have a high melting point or a poor heat resistance, they have the drawback that the temperature range applicable to analysis is limited.

In order to eliminate the above defect, the present inventors have previously provided novel optically active s-triazine derivatives which have a high heat resistance and are usable over a wide temperature range and a gas chromatographic method using them (U.S. pat. appln. Ser. No. 760,849).

However, in order to analyze the compounds having a higher boiling point, there is required an optically active stationary phase which has further superior heat resistance.

An object of the present invention is to provide novel optically active s-triazine derivatives which are useful as an optically active stationary phase for gas chromatography usable over a wide temperature range, especially at a high temperature. Another object of the invention is to provide a gas chromatographic method for the resolution and analysis of a mixture of enantiomers having an —NH— group linked to the asymmetric carbon atom which comprises using said novel s-striazine derivative as a stationary phase for the gas chromatography.

These and other objects of the invention will be apparent from the description hereinafter.

The optically active stationary phase according to the present invention is an optically active s-triazine derivative having at least two asymmetric carbon atoms of the general formula:

wherein n is 2 to 3; and X and Y are the same or different and are each a member selected from the group consisting of the groups:

wherein m is 1 to 3; and $R_1$, $R_2$, $R_3$, $R_4$, $R_5$ and $R_6$ are the same or different and are each an alkyl having 1 to 12 carbon atoms, a cycloalkyl having 5 to 6 carbon atoms, phenyl or benzyl. For example, the compound No. 4 in Table 1 has a low melting point and a high heat resistance, and hence, it can be used for the analysis over a wide temperature range such as 70° to 170° C. This compound is very suitable for the resolution and analysis of the mixture of enantiomers having an —NH— group linked to an asymmetric carbon atom, such as N-trifluoroacetyl-dl-α-naphthylethylamine, because the peaks are well separable and have a sharp and highly symmetric shape. Further, the compound No. 9 in Table 1 is superior in the heat resistance so that it can stably be used even at 180° C. The compound is characterized by applicability to the gas chromatographic resolution and analysis of a mixture of enantiomers having a high boiling point, such as N,N′-di-trifluoroacetyl-dl-lysine-ethyl ester.

In the present specification, the term "alkyl" denotes a straight or branched alkyl having 1 to 12 carbon atoms such as methyl, ethyl, propyl, isopropyl, butyl, isobutyl, sec-butyl, tert-butyl, pentyl, hexyl, heptyl, octyl, decyl, undecyl or dodecyl, and "cycloalkyl" denotes a cycloalkyl having 5 to 6 carbon atoms such as cyclopentyl or cyclohexyl.

In the preferred embodiment of the optically active s-triazine derivative of the formula (I), $R_1$, $R_2$, $R_3$, $R_4$, $R_5$ and $R_6$ are the same or different and are each an alkyl having 2 to 8 carbon atoms, cyclohexyl or benzyl, more preferably $R_1$ and $R_3$ are the same or different and are each isopropyl or benzyl, $R_2$ and $R_4$ are the same or different and are each isopropyl or cyclohexyl, $R_5$ is n-octyl or cyclohexyl and $R_6$ is ethyl. Particularly suitable optically active s-triazine derivatives having at least two asymmetric carbon atoms are represented by the following formulae:

The s-triazine derivatives of the general formula (I) of the present invention can be prepared by the well-known methods disclosed, for example, in Journal of the American Pharmaceutical Association, Vol. XIL, No. 7, 461–463, which comprises reacting a polypeptide ester with cyanuric chloride in an inert solvent in the presence of an acid-binding agent such as sodium carbonate or potassium carbonate and, if necessary, reacting the resulting s-triazine substituted with one or two members selected from amino acid esters with an alcohol or amines.

Examples of the compounds according to the present

Table 1

| No. | Compound | Elementary analysis Calcd. | Elementary analysis Found | Optical rotation | Melt-point (°C) |
|---|---|---|---|---|---|
| 1 | (structure) | C 59.0 H 8.8 N 15.0 | C 58.7 H 8.6 N 15.4 | $[\alpha]_D^{20}$ −110.8° (c, 2.0, $CHCl_3$) | 65–67 |
| 2 | (structure) | C 68.0 H 6.5 N 10.9 | C 67.6 H 6.7 N 10.6 | $[\alpha]_D^{18}$ −34.6° (c, 2.01, $CHCl_3$) | 84–85 |
| 3 | (structure) | C 55.4 H 8.0 N 15.6 | C 54.8 H 8.1 N 15.6 | $[\alpha]_D^{20}$ −118.5° (c, 4.0, $CHCl_3$) | 89–91 |
| 4 | (structure) | C 58.4 H 8.7 N 15.4 | C 58.3 H 8.5 N 15.5 | $[\alpha]_D^{20}$ −111.9° (c, 4.0, $CHCl_3$) | 67–69 |
| 5 | (structure) | C 60.8 H 9.1 N 16.2 | C 60.3 H 9.2 N 16.2 | $[\alpha]_D^{20}$ −156.6° (c, 3.0, $CHCl_3$) | 103–105 |
| 6 | (structure) | C 61.6 H 9.5 N 15.5 | C 62.0 H 9.8 N 15.7 | $[\alpha]_D^{20}$ −106.4° (c, 0.79, $CHCl_3$) | 55–56 |

Table 1-continued

| No. | Compound | Elementary analysis Calcd. | Found | Optical rotation | Melting point (°C) |
|---|---|---|---|---|---|
| 7 | CH₃-CHOOC-CH-NHCO-CH-NH-C(=N)-N=C-NH-CH-CONH-CH-COOCH(CH₃)₂ structure with isopropyl groups | C 59.2 H 8.9 N 14.9 | C 58.7 H 9.0 N 14.7 | $[\alpha]_D^{20}$ −159.0° (c, 1.0, CHCl₃) | 194-195 |
| 8 | Similar triazine structure with isopropyl ester groups | C 59.3 H 8.9 N 14.8 | C 59.5 H 9.1 N 14.8 | $[\alpha]_D^{20}$ −157.0° (c, 1.7, CHCl₃) | 257-258 |
| 9 | Triazine structure with O—C₂H₅ group and isopropyl ester groups | C 58.9 H 8.8 N 15.1 | C 58.6 H 9.0 N 15.1 | $[\alpha]_D^{15}$ −110.7° (c, 2.65, CHCl₃) | 141-142 |

For the application of the optically active stationary phase according to the present invention to the gas chromatographic resolution and analysis, the conventional methods, for example, the packed column system which uses a column packed with the stationary phase supported on stationary phase supports, or the capillary column system which uses a column having its inner surface coated with the stationary phase, can be utilized too. The optically active stationary phase according to the present invention can be applied both to the analysis and preparation of a mixture of enantiomers having an —NH— group linked to an asymmetric carbon atom. For the analytical purpose, the capillary column system is preferred in general, while for the preparative purpose the packed column system is suitable.

A more complete understanding of the nature and the objects of the invention is afforded by reference to the accompanying drawings in connection with the following description in which:

FIG. 1-A shows the gas chromatogram obtained by the analysis of the enantiomeric mixture of N-trifluoroacetyl-dl-alanine t-butyl ester using the stationary phase in Example 1;

FIG. 1-B shows the gas chromatogram obtained by the analysis of the enantiomeric mixture of N-trifluoroacetyl-dl-α-naphthylethylamine using the stationary phase in Example 1;

The present invention will be illustrated with reference to the following examples, which are only given for the purpose of illustration and are not to be interpreted as limiting the invention thereto.

EXAMPLE 1

To 30 ml of anhydrous tetrahydrofuran, 2 g (0.009 mole) of N-t-butyroxycarbonyl-l-valine, 1.8 g (0.009 mole) of l-valine isopropyl ester hydrochloride, 1.24 g (0.009 mole) of 1-hydroxybenzotriazole and 1.02 ml (0.008 mole) of N-ethylmorpholine were added in this order. The mixture was cooled to 0° C. and a solution of 1.9 g (0.009 mole) of dicyclohexylcarbodiimide in 15 ml of tetrahydrofuran was dropwise added thereto with stirring. After completion of the dropwise addition, the temperature of the reaction mixture was elevated to room temperature and reacted for 6 hours with stirring. After completion of the reaction, the white precipitate was filtered off and the tetrahydrofuran was removed by evaporation. The residue obtained was dissolved in 250 ml of ethyl acetate and the resulting solution was washed successively with an aqueous solution saturated with sodium hydrogen carbonate, 2N aqueous citric acid solution, an aqueous solution saturated with sodium hydrogen carbonate and water, and then dried over anhydrous sodium sulfate. The ethyl acetate was removed by evaporation to obtain N-t-butyroxycarbonylvalyl-l-valine isopropyl ester as a pale yellow solid substance.

Next, 2.5 g (0.007 mole) of N-t-butyroxycarbonyl-l-valyl-l-valine isopropyl ester was dissolved in a small amount of methanol. The resulting solution was ice-cooled and 100 ml of 2.7N methanolic hydrochloric acid was added thereto. The mixture was stirred for 2 hours at room temperature and the methanol was removed by evaporation. Petroleum ether was added to the oily residue obtained and the precipitated white solid substance, l-valyl-l-valine isopropyl ester hydrochloride, was filtered.

Next, 40 ml of acetone was added to 1.39 g (0.0047 mole) of l-valyl-l-valine isopropyl ester hydrochloride and 20 ml of an acetone solution containing 0.43 g (0.0024 mole) of cyanuric chloride was dropwise added to the resulting solution at 0° to 5° C. with stirring. After completion of the dropwise addition, the temperature of the reaction mixture was elevated to room temperature. Next, 1.5 g of anhydrous sodium carbonate was added to the mixture, and the mixture was reacted at 50° to 55° C. for 20 hours.

After completion of the reaction, the white precipitate was filtered off and the acetone was removed by evaporation to obtain the compound No. 3 in Table 1. The compound was dissolved in dioxane and excess ethyl alcohol was added thereto. The resulting solution was stirred under reflux for 50 hours in the presence of anhydrous sodium carbonate. After completion of the reaction, the white precipitate was filtered off and the dioxane and ethyl alcohol were removed by evaporation to obtain the compound No. 4 in Table 1.

Figure 1:
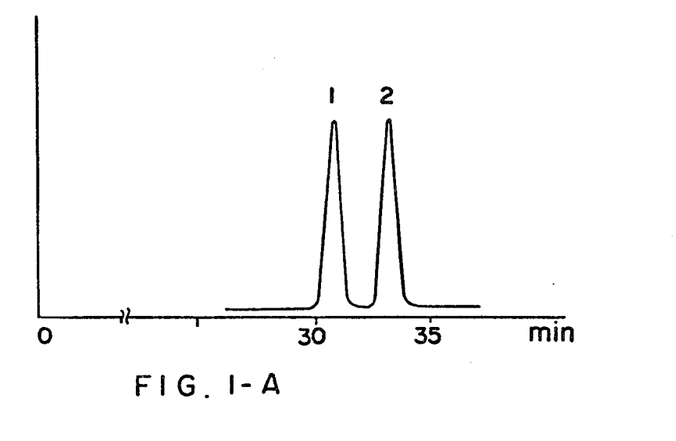

The compound thus obtained was coated on the inner surface of the glass capillary column of 0.25 mm in internal diameter and 30 m in length and N-trifluoroacetyl-dl-alanine t-butyl ester was analyzed under the following test conditions to obtain the gas chromatogram as shown in FIG. 1-A.

Column temperature: 100° C.
Detector: FID
Inlet temperature: 250° C.
Carrier gas: He
Split ratio: 1:105

In said gas chromatogram, the peak 1 corresponds to N-trifluoroacetyl-d-alanine t-butyl ester and the peak 2 corresponds to N-trifluoroacetyl-l-ananine t-butyl ester, respectively.

The time required for all the l-enantiomer to emerge from the column was about 34 minutes.

Using the same column as above, N-trifluoroacetyl-dl-α-naphthylethylamine was analyzed under the following test conditions to obtain the gas chromatogram as shown in FIG. 1-B.

Column temperature: 170° C.
Detector: FID
Inlet temperature: 200° C.
Carrier gas: He
Split ratio: 1:114

In said gas chromatogram, the peak 1 corresponds to N-trifluoroacetyl-d-α-naphthylethylamine and the peak 2 corresponds to N-trifluoroacetyl-l-α-naphthylethylamine, respectively.

The time required for all the l-enantiomer to emerge from the column was about 20 minutes.

EXAMPLE 2

Thirty milliliters of acetone was added to 0.5 g (0.0017 mole) of l-valyl-l-valine isopropyl ester hydrochloride obtained in the same manner as in Example 1, and then 15 ml of an acetone solution containing 0.31 g (0.0017 mole) of cyanuric chloride was added dropwise thereto at 0° to 5° C. with stirring. After completion of the dropwise addition, the temperature of the reaction mixture was elevated to room temperature. Next, 0.5 g of sodium hydrogen carbonate was added thereto and the mixture was reacted at room temperature for 10 hours.

After completion of the reaction, the white precipitate was filtered off and the acetone was removed by evaporation to obtain the white solid substance. Then, 0.3 g (0.0007 mole) of this substance was dissolved in dioxane and 0.35 g (0.0022 mole) of l-valine isopropyl ester and 0.5 g (0.006 mole) of sodium hydrogen carbonate were added to the resulting solution. The mixture was stirred at 50° to 60° C. for 1 hour and then stirred under reflux at 100° C. for 16 hours. After completion of the reaction, the white precipitate was filtered off and the dioxane was removed by evaporation to obtain the compound No. 1 in Table 1.

Figure 2:
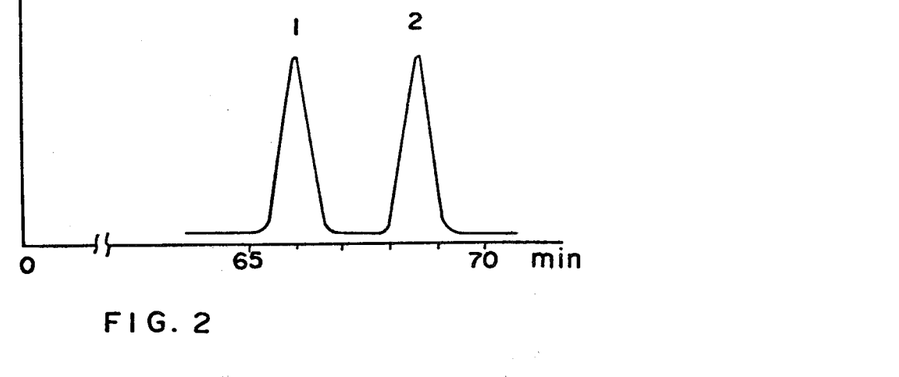
FIG. 2 shows the gas chromatogram obtained by the analysis of the enantiomeric mixture of N-pentafluoropropionyl-dl-α-phenylethylamine using the stationary phase in Example 2.

This compound was coated on the inner surface of the capillary column of 0.25 mm in internal diameter and 30 m in length and N-pentafluoropropionyl-dl-α-phenylethylamine was analyzed under the following test conditions to obtain the gas chromatogram as shown in FIG. 2.

Column temperature: 110° C.
Detector: FID
Inlet temperature: 250° C.
Carrier gas: He
Split ratio: 1:102

In said gas chromatogram, the peak 1 corresponds to N-pentafluoropropionyl-d-α-phenylethylamine and the peak 2 corresponds to N-pentafluoropropionyl-l-α-phenylethylamine. The time required for all the l-enantiomer to emerge from the column was about 69 minutes.

EXAMPLE 3

The compound No. 3 in Table 1 was obtained in the same manner as in Example 1.

Figure 3:
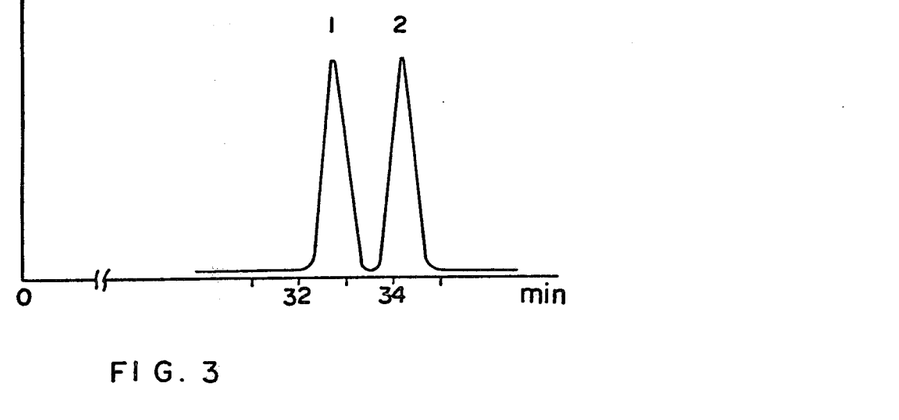
FIG. 3 shows the gas chromatogram obtained by the analysis of the enantiomeric mixture of N-trifluoroacetyl-dl-α-phenylethylamine using the stationary phase in Example 3.

Using the same column as in Example 1, wherein the compound No. 3 was coated on the inner surface of the column, N-trifluoroacetyl-dl-α-phenylethylamine was analyzed under the following test conditions to obtain the gas chromatogram as shown in FIG. 3.

Column temperature: 110° C.
Detector: FID
Inlet temperature: 200° C.
Carrier gas: He
Split ratio: 1:117

In said chromatogram, the peak 1 corresponds to N-trifluoroacetyl-d-α-phenylethylamine and the peak 2 corresponds to N-trifluoroacetyl-l-α-phenylethylamine. The time required for all the l-enantiomer to emerge from the column was about 35 minutes.

EXAMPLE 4

The compound No. 3 in Table 1 was obtained in the same manner as in Example 1.

This compound was dissolved in dioxane and excess cyclohexylamine was added thereto. The resulting solution was stirred under reflux for 27 hours in the presence of anhydrous sodium carbonate.

After completion of the reaction, the white precipitate was filtered off and dioxane and excess cyclohexylamine were removed by evaporation to obtain the compound No. 5 in Table 1.

Figure 4:
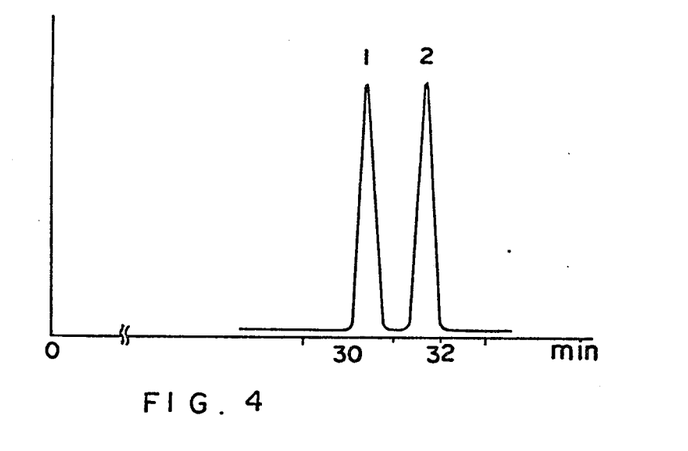
FIG. 4 shows the gas chromatogram obtained by the analysis of the enantiomeric mixture of N-pentafluoropropionyl-dl-α-naphthylethylamine using the stationary phase in Example 4.

Using the same column as in Example 1, wherein the compound No. 5 was coated on the inner surface of the column, N-pentafluoropropionyl-dl-α-naphthylethylamine was analyzed under the following test conditions to obtain the gas chromatogram as shown in FIG. 4.

Column temperature: 165° C.
Detector: FID
Inlet temperature: 250° C.
Carrier gas: He
Split ratio: 1:110

In the chromatogram, the peak 1 corresponds to N-pentafluoropropionyl-d-α-naphthylethylamine and the peak 2 corresponds to N-pentafluoropropionyl-l-α-naphthylethylamine. The time required for all the l-enantiomer to emerge from the column was about 32 minutes.

EXAMPLE 5

The compound No. 6 in Table 1 was obtained in the same manner as in Example 4 except that n-octylamine was used in place of cyclohexylamine and the solution was stirred under reflux for 40 hours.

Figure 5:
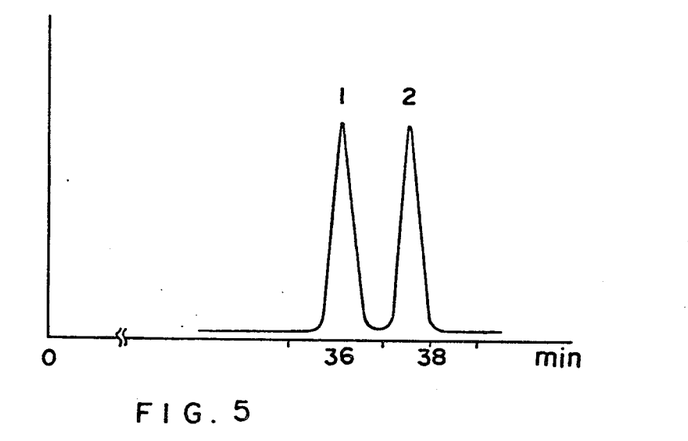
FIG. 5 shows the gas chromatogram obtained by the analysis of the enantiomeric mixture of N-trifluoroacetyl-dl-α-naphthylethylamine using the stationary phase in Example 5.

Using the same column as in Example 1, wherein the compound No. 6 was coated on the inner surface of the column, N-trifluoroacetyl-dl-α-naphthylethylamine was analyzed under the following test conditions to obtain the gas chromatogram as shown in FIG. 5.

Column temperature: 160° C.
Detector: FID
Inlet temperature: 200° C.
Carrier gas: He
Split ratio: 1:111

In said chromatogram, the peak 1 corresponds to N-trifluoroacetyl-d-α-naphthylethylamine and the peak 2 corresponds to N-trifluoroacetyl-l-α-naphthylethylamine. The time required for all the l-enantiomer to emerge from the column was about 38 minutes.

EXAMPLE 6

To 60 ml of anhydrous tetrahydrofuran, 4.35 g (0.020 mole) of N-t-butyroxycarbonyl-l-valine, 6.20 g (0.021 mole) of l-valyl-l-valine isopropylester hydrochloride obtained in the same manner as in Example 1, 2.70 g (0.020 mole) of 1-hydroxybenzotriazole an 2.07 g (0.018 mole) of N-ethylmorpholine were added in this order. The mixture was cooled to 0° C. and a solution of 4.13 g (0.020 mole) of N,N'-dicyclohexylcarbodiimide in 20 ml of tetrahydrofuran was dropwise added thereto with stirring. After completion of the dropwise addition, the temperature of the reaction mixture was elevated to room temperature and the mixture was reacted for 9 hours with stirring. After completion of the reaction, the white precipitate was filtered off and the tetrahydrofuran was removed by evaporation. The residue obtained was dissolved in 100 ml of ethyl acetate and the resulting solution was washed successively with an aqueous solution saturated with sodium carbonate, 2N aqueous citric acid solution, an aqueous solution saturated with sodium bicarbonate and water, and then dried over anhydrous sodium sulfate. The ethyl acetate was removed by evaporation to obtain N-t-butyroxycarbonyl-l-valyl-l-valyl-l-valine isopropyl ester as a white solid substance.

Next, 9.26 g. (0.020 mole) of N-t-butyroxycarbonyl-l-valyl-l-valyl-l-valine isopropyl ester was dissolved in a small amount of dioxane. The resulting solution was ice-cooled and 300 ml of 3N HCl/dioxane solution was added thereto. The mixture was stirred for 7.5 hours at room temperature and the dioxane was removed by evaporation to obtain l-valyl-l-valyl-l-valine isopropyl ester hydrochloride as a white solid substance.

7.040 g (0.019 mole) of l-valyl-l-valyl-l-valine isopropyl ester hydrochloride was then covered with 100 ml of ether, and thereto was added 60 ml of 1N aqueous ammonia, and the aqueous layer was extracted three times with ether. The ether layer was washed three times with water, dried over anhydrous sodium sulfate, and then ether was evaporated off to give a white solid substance.

In addition, 92.21 g (0.500 mole) of cyanuric chloride and 50.41 g (0.600 mole) of sodium hydrogen carbonate were added in this order to 800 ml (13.73 moles) of ethanol kept at 5° C. with mechanical stirring and the mixture was reacted at this temperature for 8 hours with stirring. The resulting solution was poured into 650 g of ice-water and the precipitated white substance was immediately collected by filtration with suction. The substance was washed with 200 ml of water (0° C.) two to three times and dried in a vacuum dryer. It was recrystallized from petroleum ether to give b 2,4-dichloro-6-ethoxy-s-triazine as a colorless solid substance.

Next, 20 ml of anhydrous dioxane was added to 0.65 g (0.0034 mole) of 2,4-dichloro-6-ethoxy-s-triazine and thereto was added dropwise a solution of 2.91 g (0.0081 mole) of l-valyl-l-valyl-l-valine isopropyl ester in 30 ml of dioxane at 0° to 5° C. with stirring. After completion of the dropwise addition, 0.84 g (0.010 mole) of sodium hydrogen carbonate was added thereto and the mixture was reacted at 50° C. for 6 hours.

The reaction temperature was further elevated and the mixture was refluxed with stirring for an additional 17 hours. After completion of the reaction, the white precipitate was filtered off and the dioxane was removed by evaporation to give the compound No. 9 in Table 1.

Figure 6:
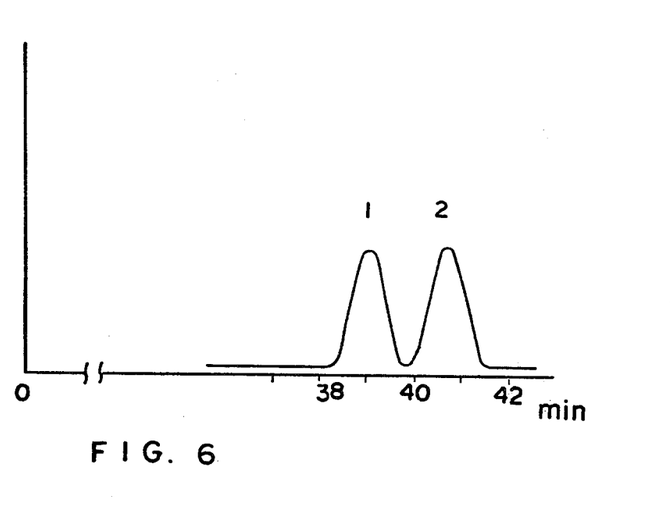
FIG. 6 shows the gas chromatogram obtained by the analysis of the enantiomeric mixture of N-trifluoroacetyl-dl-lysine ethyl ester using the stationary phase in Example 6.

Using the same column as in Example 1, wherein the compound No. 9 was coated on the surface of the column, N,N'-di-trifluoroacetyl-dl-lysine ethyl ester was analyzed under the following test conditions to obtain the gas chromatogram as shown in FIG. 6.

Column temperature: 180° C.
Detector: FID
Inlet temperature: 250° C.
Carrier gas: He
Split ratio: 1:110

In said gas chromatogram, the peak 1 corresponds to N,N'-di-trifluoroacetyl-d-lysine ethyl ester and the peak 2 corresponds to N,N'-di-trifluoroacetyl-l-lysine ethyl ester. The time required for all the l-enantiomer to emerge from the column was about 41 minutes.

What is claimed is:

1. In a gas chromatographic method for the resolution and analysis of a mixture of enantiomers having an —NH— group linked to an asymmetric carbon atom comprising reacting said mixture with an optically active reagent to form the diastereomers and resolving and analyzing the diastereomers on an optically inactive stationary phase, the improvement which comprises using as the stationary phase an s-triazine derivative with at least two asymmetric carbon atoms of the following general formula:

wherein n is 2 or 3; and X and Y are the same or different and are each a member selected from the group consisting of the groups:

wherein m is 1 to 3; and $R_1$, $R_2$, $R_3$, $R_4$, $R_5$ and $R_6$ are the same or different and are each an alkyl having 1 to 12 carbon atoms, a cycloalkyl having 5 to 6 carbon atom, phenyl or benzyl.

2. The method according to claim 1, wherein $R_1$, $R_2$, $R_3$, $R_4$, $R_5$ and $R_6$ are the same or different and are each an alkyl having 2 to 8 carbon atoms, cyclohexyl or benzyl.

3. The method according to claim 1, wherein $R_1$ and $R_3$ are the same or different and are each isopropyl or benzyl, $R_2$ and $R_4$ are the same or different and are each isopropyl or cyclohexyl, $R_5$ is n-octyl or cyclohexyl and $R_6$ is ethyl.

4. The method according to claim 1, wherein the s-triazine derivative has the formula:

5. The method according to claim 1, wherein the s-triazine derivative has the formula:

6. The method according to claim 1, wherein the s-triazine derivative has the formula:

* * * * *